(12) United States Patent
Holmes et al.

(10) Patent No.: US 10,926,079 B2
(45) Date of Patent: *Feb. 23, 2021

(54) NEURO-STEM CELL STIMULATION AND GROWTH ENHANCEMENT WITH IMPLANTABLE NANODEVICE

(71) Applicant: INTERNATIONAL BUSINESS MACHINES CORPORATION, Armonk, NY (US)

(72) Inventors: Steven J. Holmes, Ossining, NY (US); Qinghuang Lin, Yorktown Heights, NY (US); Emily R. Kinser, Poughkeepsie, NY (US); Nathan P. Marchack, New York, NY (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/573,533

(22) Filed: Sep. 17, 2019

(65) Prior Publication Data
US 2020/0009368 A1   Jan. 9, 2020

Related U.S. Application Data

(62) Division of application No. 15/811,023, filed on Nov. 13, 2017, now Pat. No. 10,583,282.

(51) Int. Cl.
*A61N 1/04* (2006.01)
*A61K 38/18* (2006.01)
(Continued)

(52) U.S. Cl.
CPC .............. *A61N 1/04* (2013.01); *A61B 5/4839* (2013.01); *A61K 38/185* (2013.01); *A61N 1/05* (2013.01);
(Continued)

(58) Field of Classification Search
CPC .................................................... A61B 5/4839
(Continued)

(56) References Cited

U.S. PATENT DOCUMENTS 7,844,345 B2   11/2010  Boling et al.
8,003,192 B2   8/2011   Hong et al.
(Continued)

OTHER PUBLICATIONS

List of IBM Patents or Patent Applications Treated as Related dated Sep. 17, 2019, 2 pages.
(Continued)

*Primary Examiner* — Brent T O'Hern
(74) *Attorney, Agent, or Firm* — Tutunjian & Bitetto, P.C.; L. Jeffrey Kelly

(57) ABSTRACT

A nanodevice includes an array of metal nanorods formed on a substrate. An electropolymerized electrical conductor is formed over tops of a portion of the nanorods to form a reservoir between the electropolymerized conductor and the substrate. The electropolymerized conductor includes pores that open or close responsively to electrical signals applied to the nanorods. A cell loading region is disposed in proximity of the reservoir, and the cell loading region is configured to receive stem cells. A neurotrophic dispensing material is loaded in the reservoir to be dispersed in accordance with open pores to affect growth of the stem cells when in vivo.

6 Claims, 10 Drawing Sheets

(51) Int. Cl.
*A61B 5/00* (2006.01)
*B82Y 15/00* (2011.01)
*A61N 1/375* (2006.01)
*A61N 1/05* (2006.01)
*A61N 1/08* (2006.01)

(52) U.S. Cl.
CPC .............. *A61N 1/08* (2013.01); *A61N 1/375* (2013.01); *B82Y 15/00* (2013.01); *A61B 2562/028* (2013.01); *A61L 2400/12* (2013.01)

(58) Field of Classification Search
USPC .......................................................... 428/98
See application file for complete search history.

(56) References Cited

U.S. PATENT DOCUMENTS

| | | | |
|---|---|---|---|
| 8,175,711 | B2 | 5/2012 | Demarais et al. |
| 8,263,002 | B1 | 9/2012 | Chow et al. |
| 8,465,484 | B2 | 6/2013 | Davalos et al. |
| 9,070,492 | B2 | 6/2015 | Yarmush et al. |
| 10,583,282 | B2 * | 3/2020 | Holmes ................. B82Y 15/00 |
| 10,694,972 | B2 | 6/2020 | Davalos et al. |
| 2006/0189018 | A1 | 8/2006 | Yi et al. |
| 2010/0003316 | A1 | 1/2010 | Vo Dinh et al. |
| 2010/0233226 | A1 | 9/2010 | Ferain et al. |
| 2012/0088994 | A1 | 4/2012 | Bode et al. |
| 2012/0263793 | A1 * | 10/2012 | Vitaliano ............. G01N 21/658 424/490 |
| 2013/0144365 | A1 | 6/2013 | Kipke et al. |
| 2014/0330244 | A1 | 11/2014 | Hyde et al. |
| 2014/0336487 | A1 | 11/2014 | Wang et al. |
| 2014/0371564 | A1 | 12/2014 | Anikeeva et al. |
| 2015/0032137 | A1 | 1/2015 | Wagner et al. |
| 2020/0009368 | A1 * | 1/2020 | Holmes ................ A61K 38/185 |
| 2020/0108244 | A1 | 4/2020 | Holmes et al. |

OTHER PUBLICATIONS

Huang, Y. et al., "Electrical stimulation elicits neural stem cells activation: new perspectives in CNS repair" Front. Hum. Neurosci. (Oct. 2015) pp. 1-9, vol. 9, Article 586.

Jeon, G. et al., "Electrically Actuatable Smart Nanoporous Membrane for Pulsatile Drug Release" Nano Letters (Jan. 2011) pp. 1284-1288, vol. 11.

Beebe, S.J., Nanosecond pulsed electric field (nsPEF) effects on cells and tissues: apoptosis induction and tumor growth inhibition IEEE Transactions on Plasma Science (Feb. 2002) pp. 286-292, vol. 30, No. 1.

List of IBM Patents or Patent Applications Treated as Related dated Nov. 13, 2017, 2 pages.

U.S. Office Action issued in U.S. Appl. No. 15/602,363, dated May 16, 2019, pp. 1-18.

Gu, Yan, et al., "Understanding nanoparticle drug delivery from rotational dynamics and behaviors of functionalized gold nanorods on live cell membranes," Biophys. J, 2011, pp. 473a-473a, 100,3.

Kim, Kibeom, et al., "Externaly controlled drug release using a gold nanorod contained composite membrane," Nanoscale, 2016, pp. 11949-11955, 8.

U.S. Final Office Action issued in U.S. Appl. No. 15/602,363, dated Oct. 21, 2019, 14 pages.

U.S. Notice of Allowance issued in U.S. Appl. No. 15/810,483, dated Oct. 25, 2019, 36 pages.

U.S. Office Action issued in U.S. Appl. No. 15/602,363, dated Mar. 6, 2020, 12 pages.

U.S. Office Action issued in U.S. Appl. No. 16/573,644, dated Jul. 6, 2020, 27 pages.

US Final Office Action issued in U.S. Appl. No. 15/602,363: dated Oct. 2, 2020 pp. 1-17.

* cited by examiner

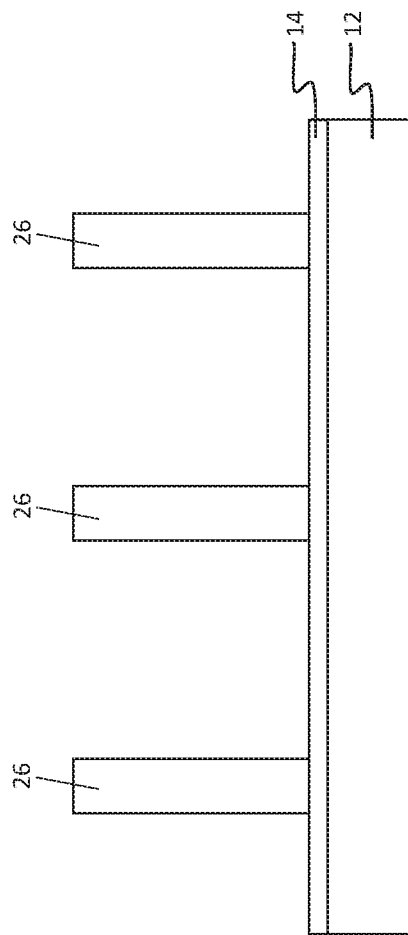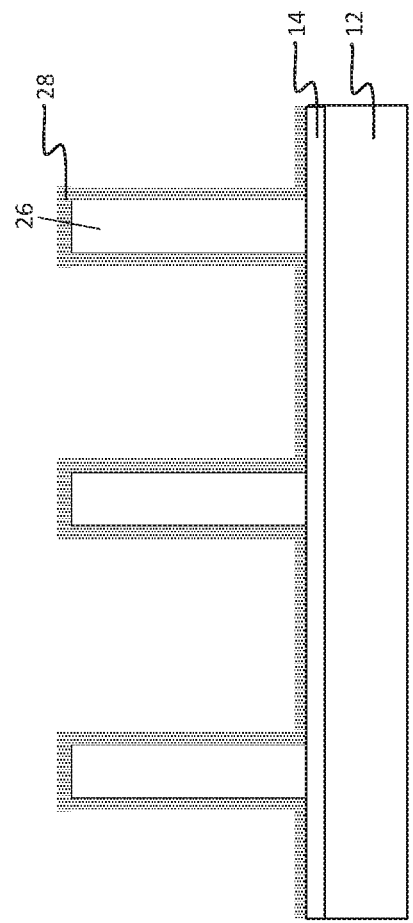
FIG. 4
FIG. 5

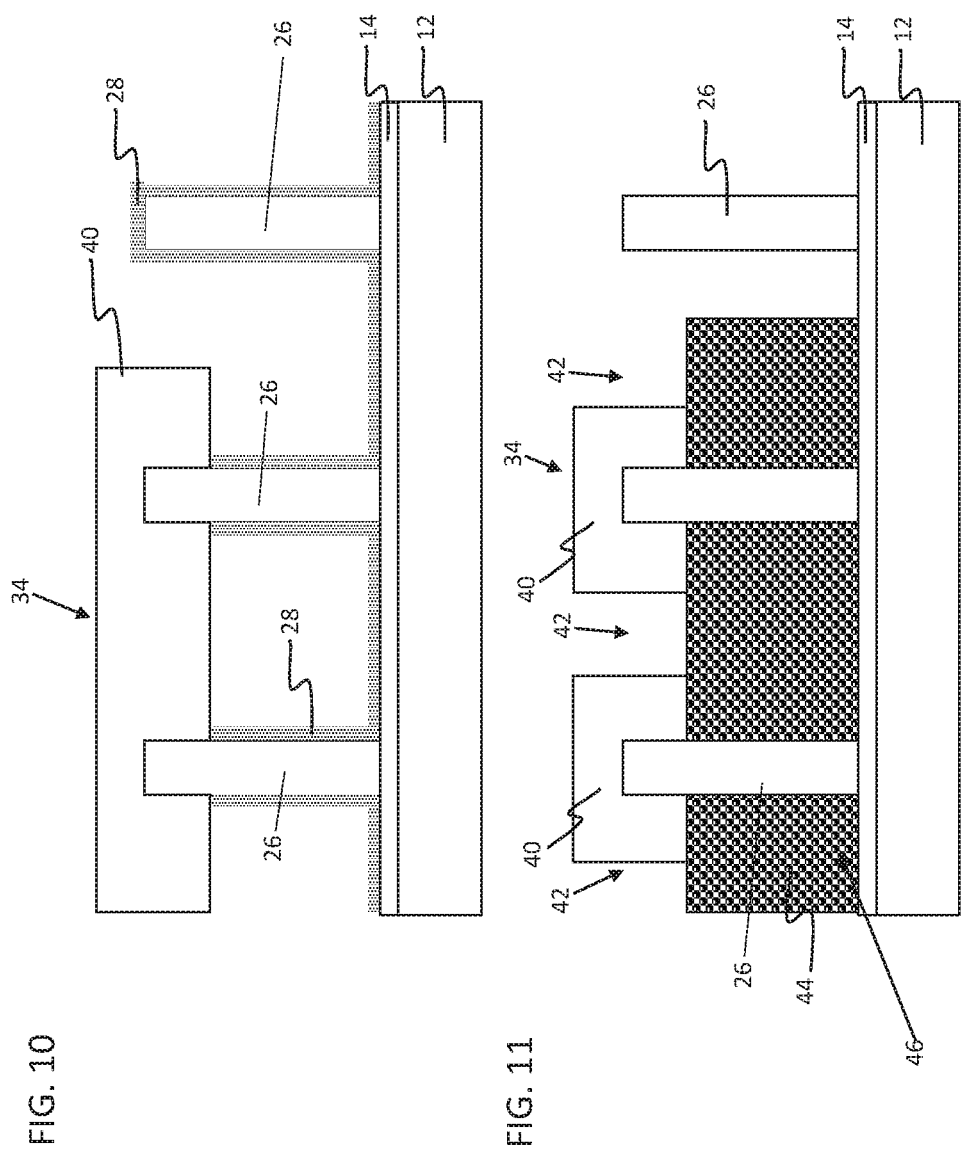

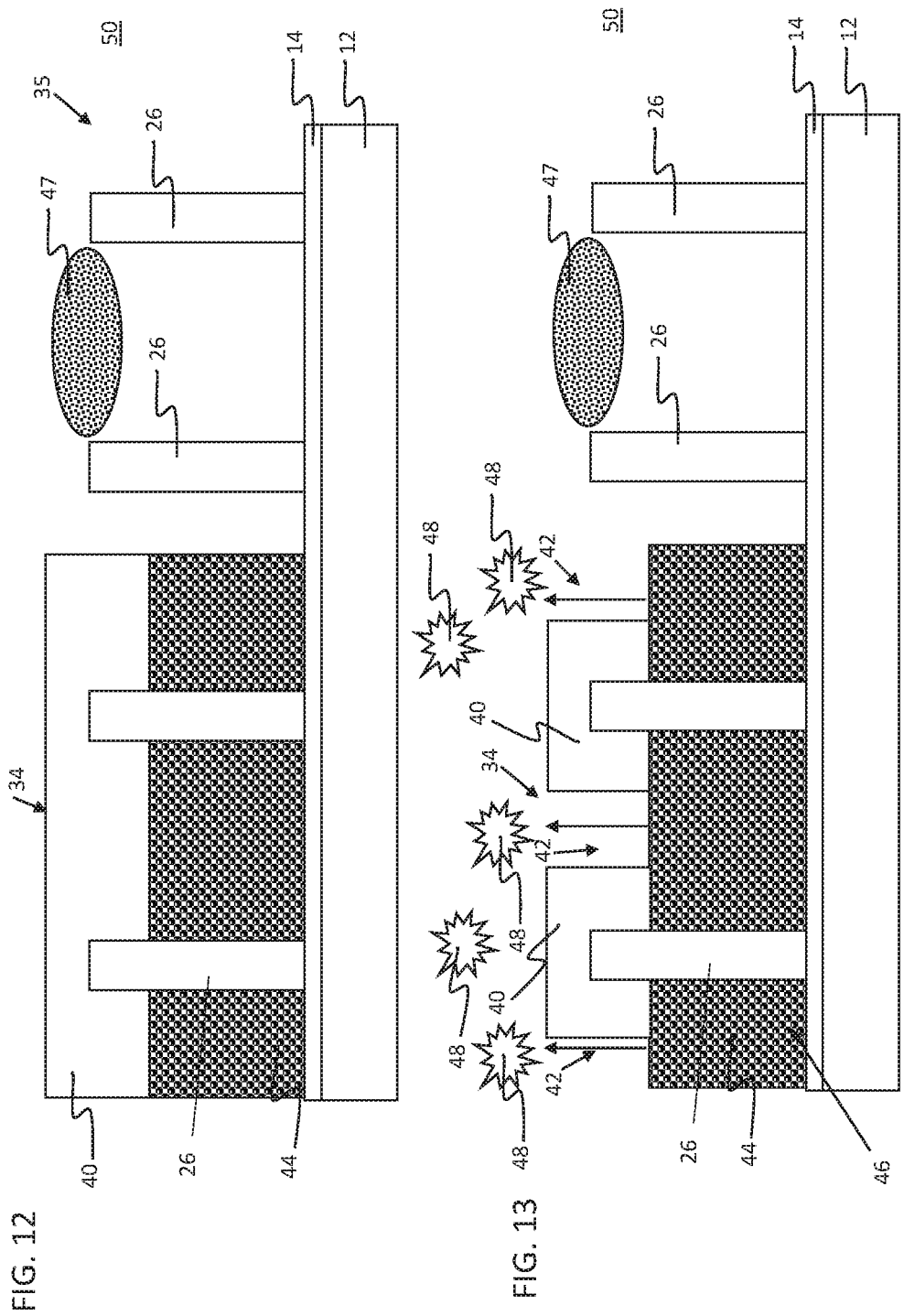

NEURO-STEM CELL STIMULATION AND GROWTH ENHANCEMENT WITH IMPLANTABLE NANODEVICE

BACKGROUND

Technical Field

The present invention generally relates to implantable nanodevices, and more particularly to devices and methods to control molecular interactions at a device electrode by releasing materials factor to affect cell growth.

Description of the Related Art

Neuro-degenerative disease can be treated with neuro stem cells, but an effective method of placing the stem cells in a proper location, stimulating their differentiation into functional nerve cells, and providing materials for their healthy growth remains a problem.

SUMMARY

In accordance with an embodiment of the present invention, a nanodevice includes an array of metal nanorods formed on a substrate. An electropolymerized electrical conductor is formed over tops of a portion of the nanorods to form a reservoir between the electropolymerized conductor and the substrate. The electropolymerized conductor includes pores that open or close responsively to electrical signals applied to the nanorods. A cell loading region is disposed in proximity of the reservoir, and the cell loading region is configured to receive stem cells. A neurotrophic dispensing material is loaded in the reservoir to be dispersed in accordance with open pores to affect growth of the stem cells when in vivo.

Another nanodevice includes an array of metal nanorods formed on a substrate, the array of metal nanorods being grouped into a first region and a second region. The first region includes first nanorods such that upon activation of the first nanorods an electric field consistent with promoting stem cell growth is achieved. The second region includes second nanorods configured to activate an electropolymerized electrical conductor formed over tops of the second nanorods to form a reservoir between the electropolymerized electrical conductor and the substrate. The electropolymerized electrical conductor includes pores that open or close responsively to electrical signals applied to the second nanorods to release a growth factor.

A method for growing or differentiating in vivo stem cells includes providing a reservoir with a cell growth promoter, the reservoir being formed between an electropolymerized electrical conductor and a metal layer on a nanodevice, the electropolymerized electrical conductor including pores that open or close responsively to electrical signals applied to first nanorods extending from the metal layer of a nanodevice; providing at least one stem cell on second nanorods of the nanodevice; placing the nanodevice in vivo; electrically stimulating cell growth or differentiation of the at least one stem cell on the second nanorods; and dispensing the growth factor through the electropolymerized electrical conductor by applying a first voltage to the first nanorods to affect further growth of the stem cells.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 4 is a cross-sectional view showing a new cross-section with three nanorods formed on a substrate in accordance with an embodiment of the present invention;

FIG. 5 is a cross-sectional view showing the substrate of FIG. 4 having an atomic layer deposited coating formed on the metal layer and the nanorods in accordance with an embodiment of the present invention;

FIG. 10 is a cross-sectional view showing the substrate of FIG. 9 having an electropolymerized conductor formed on the exposed nanorods in accordance with an embodiment of the present invention;

FIG. 11 is a cross-sectional view showing the substrate of FIG. 10 having pores of the electropolymerized conductor opened to load a dispensing material into a reservoir in accordance with an embodiment of the present invention;

FIG. 12 is a cross-sectional view showing the substrate of FIG. 11 prepared for deployment in vivo with the dispensing material and cells loaded on the device in accordance with an embodiment of the present invention;

FIG. 13 is a cross-sectional view showing the substrate of FIG. 12 having the dispensing material deployed through open pores in the electropolymerized conductor in accordance with an embodiment of the present invention;

DETAILED DESCRIPTION

Figure 1:
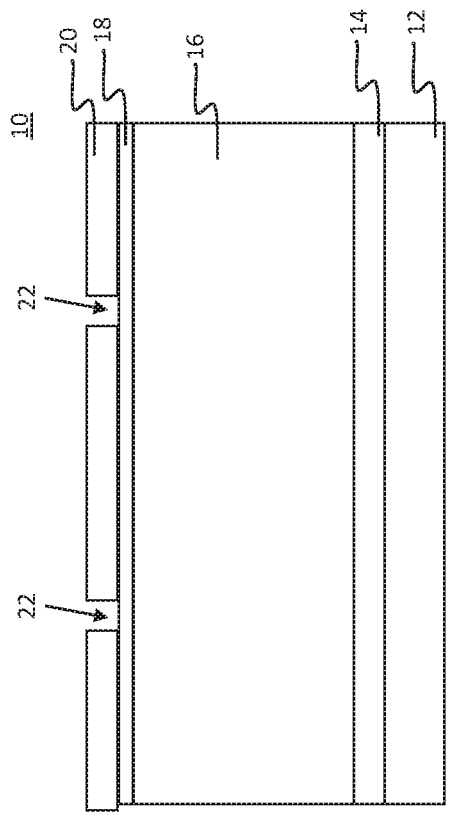
FIG. 1 is a cross-sectional view showing a substrate having a metal layer, organic planarizing layer, hard mask layer and patterned resist formed thereon for forming nanorods in accordance with an embodiment of the present invention.

In accordance with embodiments of the present invention, an implantable nano-device can be created to provide effective methods for placing cells (such as e.g., stem cells) in a proper location, stimulating their differentiation into functional nerve cells, and providing materials for their healthy growth. The nano-devices can solve these problems by creating structures for electrically functional nano-pillar electrodes (also referred to as electrodes or nanorods) across a portion of a device substrate and creating structures for nano-reservoirs of growth factor with electrically controlled release in adjacent portions of the device substrate.

In one embodiment, the nano-pillar electrodes or nanoelectrodes can be seeded with neuro stem cells. The nanodevice can be implanted into a desired region of neural tissue. The growth of the stem cells can be activated by electrical stimulation. Timed release of the growth factor can be appropriately activated into growth regions from the nano-reservoirs on the nanodevice.

In one embodiment, the nanodevices employ electrodes for detection of neural activity, such as voltage changes around active neurons or concentration levels of neurotransmitters. The electrodes can be formed as nanorods. A cell growth promoting mechanism can be employed to stimulate cellular growth from portions of a sensor or neurosensor by applying appropriate chemicals or growth promoters in specific regions of the device.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGs. It will be understood that the spatially relative terms are intended to encompass different orientations of the device in use or operation in addition to the orientation depicted in the FIGs. For example, if the device in the FIGs. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a partially fabricated nanodevice 10 is shown in accordance with one embodiment. The device 10 includes a substrate 12 having one or more layers formed thereon. The substrate 12 can include any suitable substrate structure, e.g., a bulk semiconductor, a semiconductor-on-insulator (SOI) substrate, etc. In one example, the substrate 12 can include a silicon-containing material. Illustrative examples of Si-containing materials suitable for the substrate 12 can include, but are not limited to, Si, SiGe, SiGeC, SiC and multi-layers thereof. Although silicon is the predominantly used semiconductor material in wafer fabrication, alternative semiconductor materials can be employed as additional layers, such as, but not limited to, germanium, gallium arsenide, gallium nitride, silicon germanium, cadmium telluride, zinc selenide, etc.

Since the present embodiments provide a device that can work remotely, the device 10 can include a substrate having powered circuitry for controlling the functions of the device. In this way, the substrate 12 can include control circuitry fabricated using known semiconductor processing techniques. Components can include transistors, metal lines, capacitors, logic gates or any other electronic components that permit the control of the nanorods and other structures to be formed in subsequent steps. In one useful embodiment, bipolar junction transistors (BJT) can be employed in the circuitry formed in the substrate 12. BJT devices can be employed to generate sub-nanosecond pulsing, as will be described.

A metal layer 14 is deposited on the substrate 12 and can be employed with other components formed in the substrate 12 (e.g., a metal layer). The metal layer 14 can include a conductive but relatively inert metal, such as, e.g., Pt, Au, Ag, Cu, Ir, Ru, Rh, Re, Os, Pd, and their oxides (e.g., $IrO_2$, RuOx, etc.), although other metals, metal oxides and their alloys can be employed. The metal layer 14 can be formed by deposition using a sputtering process, chemical vapor deposition (CVD) process, atomic layer deposition (ALD), a plating process or any other suitable deposition process.

In one embodiment, an organic planarizing layer (OPL) 16 is formed on the metal layer 14. The OPL 16 can be formed by a spin-on process or other deposition process. Other dielectric layers can also be employed.

An etch stop layer or hard mask 18 can be deposited over the OPL 16. In one embodiment the etch stop layer 18 can include a metal, such as, e.g., Ti, Ta, etc. or a metallic compound such as, e.g., TiN, TaN, SiARC (a silicon containing organic ARC layer), TiARC (a titanium ARC), etc. A resist layer 20 is formed on the etch stop layer or hard mask 18. The resist layer 20 can be spun on. The resist layer 20 is patterned to form openings 22 that will be employed to form nanorods as will be described.

Figure 2:
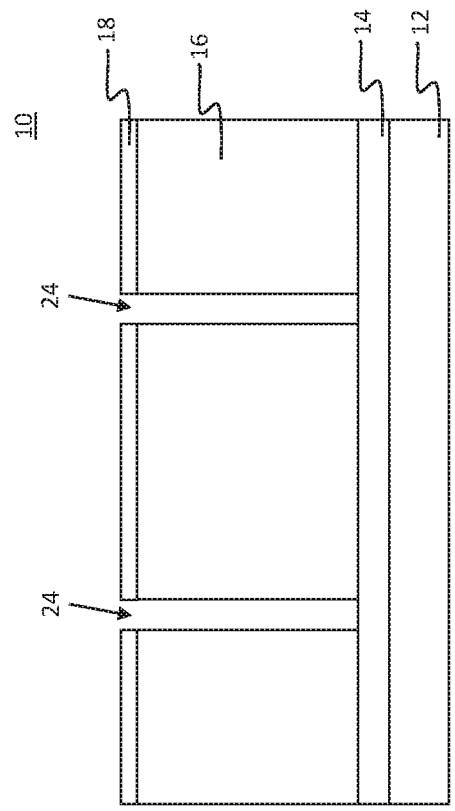
FIG. 2 is a cross-sectional view showing the substrate of FIG. 1 having the metal layer exposed by etching the organic planarizing layer in accordance with the hard mask layer and the patterned resist for forming nanorods in accordance with an embodiment of the present invention.

Referring to FIG. 2, an etch process is performed to open up the etch stop layer 18. In one embodiment, a reactive ion etch (RIE) process can be performed to expose the OPL 16 through the openings 22 and 23 (FIG. 1). Then, a RIE is performed to etch through the OPL 16 to expose the metal layer 14 and form trenches 24 in accordance with the resist 20 and/or the etch stop layer or hard mask 18. The trenches 24 provide locations for the formation of nanorods. The etch of OPL 16 should be minimized to maintain small critical dimensions (CDs) for the hole or trench 24 to be plated.

Figure 3:
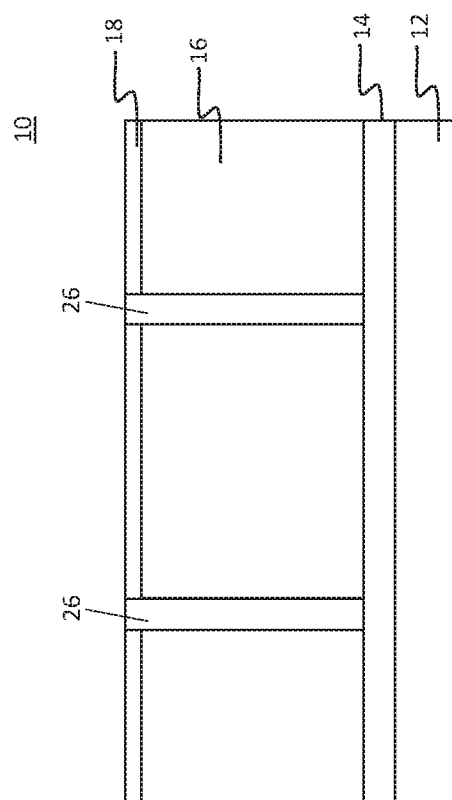
FIG. 3 is a cross-sectional view showing the substrate of FIG. 2 having nanorods plated, connecting to the metal layer and planarized to the hard mask layer in accordance with an embodiment of the present invention.

Referring to FIG. 3, a metal deposition process is performed and can include a plating process, CVD, sputtering or the like. The metal of the deposition process preferably includes a same metal as employed in metal layer 14. In one particularly useful embodiment, the metal of layer 14 and the metal used in nanorods 26 can include, e.g., Pt, Au, Ag, Cu, Ir, Ru, Rh, Re, Os, Pd, and/or their oxides (e.g., $IrO_2$, RuOx, etc.), although other metals, metal oxides and their alloys can be employed. The nanorods 26 can be annealed with the OPL 16 present or with the OPL 16 removed. If the hard mask 18 includes, e.g., Ti or TiN, the hard mask 18 can be removed with hydrogen peroxide aqueous solution, or if it is Ti oxide or TiARC, it can be removed with diluted HF, as wet etching is simpler and easier to control than planarization processes such as, e.g., a chemical mechanical polish (CMP). However, a planarization process, such as, e.g., CMP, can be employed if other hard mask materials are employed. The hard mask 18 is removed down to the OPL 16. Then, the OPL 16 can be removed by a plasma strip, e.g., oxygen plasma, forming gas plasma, with a mild wet clean to remove residues.

Referring to FIG. 4, after the removal of the OPL 16 and the anneal of the nanorods 26, the nanorods 26 are ready for continued processing. The nanorods 26 can be arranged in any configuration suitable for creating a nanodevice, e.g., an array with uniform or non-uniform spacings, etc. for chemical sensors, neurological implants or other applications.

Referring to FIG. 5, a coating 28 is formed over the nanorods 26 and metal layer 14. The coating 28 is formed using, e.g., ALD, which can be processed to prepare a protective membrane on the electrodes or nanorods 26. The membrane can include a $SiO_2$ film although other materials including organic dielectrics can be employed. In one embodiment, the coating can be formed by mixing ALD with aluminum, silicon or other materials, which can be formed in multiple layers. Each cycle of the ALD process can deposit a layer with an oxidation process thereafter to form a respective oxide (e.g., $SiO_2$ or $Al_2O_3$). In useful examples, the ALD reagent for forming Al can include $AlMe_3$ while the reagent for forming the $SiO_2$ can include $(Me_2N)_3SiH$ (where Me is a methyl group). The ALD process can include a plurality of cycles to deposit a plurality of layers. The plurality of layers can include a large number (e.g., two to several hundred). The plurality of layers form the coating 28, which can have a total thickness of between about 2 nm to about 50 nm. While other dimensions are contemplated, the coating 28 preferably includes a nanoscale thickness.

Figure 6:
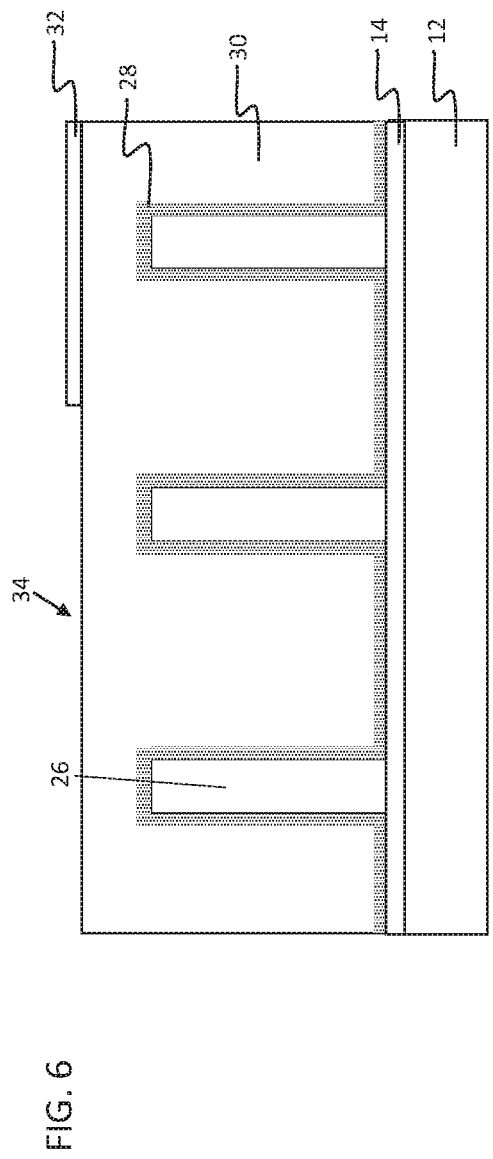
FIG. 6 is a cross-sectional view showing the substrate of FIG. 5 having another organic planarizing layer formed and a hardmask patterned thereon in accordance with an embodiment of the present invention.

Referring to FIG. 6, another OPL 30 is formed over the coating 28. The OPL 30 can be spun-on although other formation processes can be employed. Another hardmask 32 is formed on the OPL 30. The hardmask 32 can include a metal, such as, e.g., Ti, Ta, etc. or a metallic compound such as, e.g., TiN, TaN, etc. A resist (not shown) can be employed in a lithographic patterning process to pattern the etch mask 32 and protect a portion of the etch mask 32 during an etch. The etch, e.g., RIE, removes the hardmask 32 from a region 34 to open the region 34 for a growth factor reservoir to be formed.

Figure 7:
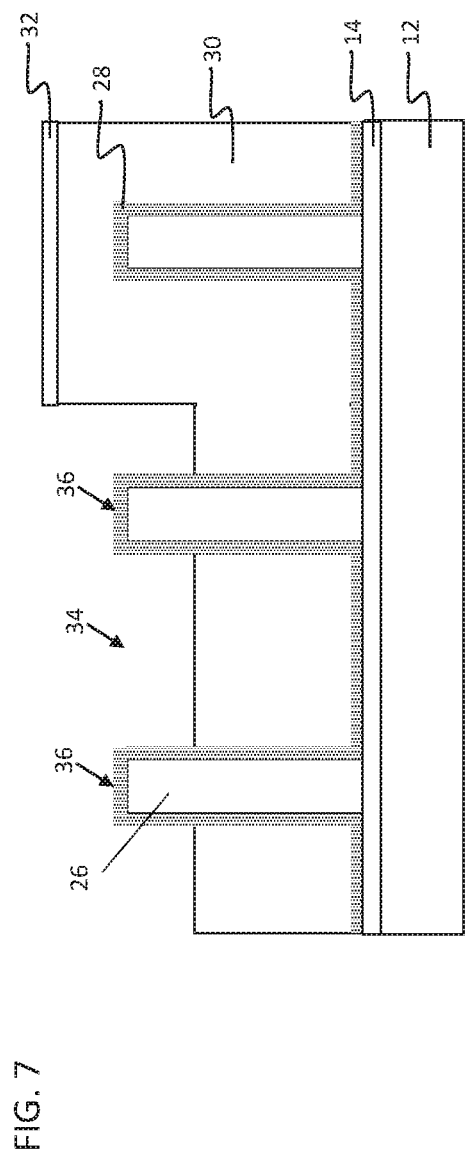
FIG. 7 is a cross-sectional view showing the substrate of FIG. 6 having the organic planarizing layer recessed to expose coated nanorods in accordance with the patterned hardmask in accordance with an embodiment of the present invention.

Referring to FIG. 7, the OPL 30 is recessed in the region 34 to expose tops 36 of the coating 28 over the nanorods 26 in the region 34. The recess process can include a RIE selective to the coating 28 and the hard mask 32.

Figure 8:
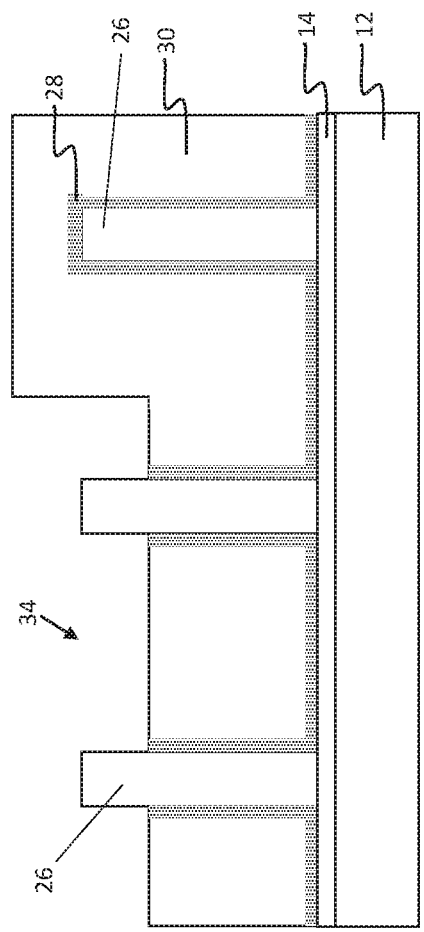
FIG. 8 is a cross-sectional view showing the substrate of FIG. 7 having the coating removed from the nanorods that was exposed by the recess and having the patterned hardmask removed in accordance with an embodiment of the present invention.

Referring to FIG. 8, a wet etch process can be performed to wet etch coating 28 from the nanorods 26 in the region 34. The wet etch can include, e.g., a diluted HF etch (DHF). Another wet etch can be performed to remove the hard mask 32 (FIG. 7) selectively relative to the nanorods 26 and the OPL 30. For example, if the hard mask 32 includes Ti, a wet etch with hydrogen peroxide ($H_2O_2$) can be employed to remove the hardmask.

Figure 9:
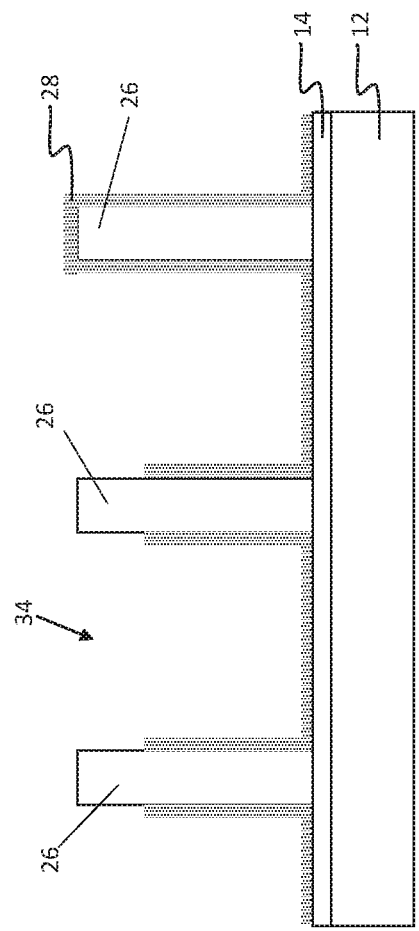
FIG. 9 is a cross-sectional view showing the substrate of FIG. 8 having the organic planarizing layer removed in accordance with an embodiment of the present invention.

Referring to FIG. 9, the OPL 30 is stripped to expose the coating 28 on the nanorods 26. The OPL 30 can be stripped using a plasma etch, such as, e.g., an $O_2$ plasma etch or $N_2/H_2$ plasma etch. The nanorods 26 which had coating 28 removed by, e.g., a wet etch previously, are exposed within the region 34.

Referring to FIG. 10, an electropolymerization process is performed to grow an electrically conductive porous polymer 40 on the exposed portions of the nanorods 26 in the region 34. In one embodiment, the porous polymer 40 forms an electrically responsive nanoporous membrane based on polypyrrole doped with a dodecylbenzenesulfonate anion (PPy/DBS) that is electropolymerized on the nanorods 26.

Electropolymerization is the process by which a polymer is formed using electrical current. The electrical current can be provided through the exposed nanorods 26 in the presence of a polymer (e.g., polypyrrole in solution). Doping can occur in-situ or after formation with the absorption of an anion or other charged molecule. The porous polymer 40 includes a regular pore size. The porous polymer 40 is configured to provide a large volume change depending on its electrochemical state, and the pore size can be actuated electrically. The porous polymer 40 is formed in its oxidation state. The porous polymer 40 includes a thickness where pores formed therein include sufficient length to pass through the entire porous polymer layer.

The coating 28 is then removed from remaining portions of the nanorods 26 by a wet etch. The wet etch can include a diluted HF etch, although other etchants can be employed. Once formed, the porous polymer 40 can have its pores opened or closed in accordance with an electrical potential applied to the polymer 40 by nanorods 26.

The porous polymer 40 can include an electropolymerized electrical conductor that includes electrically conductive polymers, such as, e.g., polypyrrole, polyanilines, poly(thiophene), poly(3,4-ethylenedioxythiophene), poly(p-phenylene sulfide), poly(p-phenylene vinylene), poly(acetylene) or combinations thereof.

Referring to FIG. 11, a reservoir 46 is formed between the polymer 40 and the metal layer 14. The polymer 40 can be electrically actuated to open pores 42 through the polymer 40, which switches to the polymer material's reduction state (as opposed to its oxidation state). The state changes can be made by a potential difference of between about 0.9 to about 1.2 volts applied to the nanorods 26. When the pores 42 are opened, a growth inhibiter or growth factor 44 can be collected within the reservoir 46. The growth factor 44 can include any useful chemical or reagent, e.g., a growth stimulator or promoter 44 can be loaded. The growth factor 44 can include any useful chemical or reagent, e.g., a neurotrophic growth factor, hormone species (e.g., steroids, etc.), metabolic stimulants, other materials, or combinations.

A growth inhibitor (44) can be employed to inhibit further growth or slow the growth of the stem cells. The growth inhibitor 44 can include any useful chemical or reagent, e.g., chemotherapy drugs (e.g., cytotoxic agents, alkylating agents, anthracyclines, cytoskeletal disruptors, epothilones, histone deacetylase inhibitors, peptide antibiotics, retinoids, etc.), hormone species (e.g., somatostatin, etc.), other materials, or combinations.

For example, the reservoir 46 can include neurotrophic growth factor or neurotrophins 48 that can include brain-derived neurotrophic factor (BDNF). BDNF is a protein that, in humans, is encoded by the BDNF gene. BDNF is a member of the neurotrophin family of growth factors, which are related to the canonical Nerve Growth Factor. Neurotrophic factors are found in the brain and its periphery. BDNF acts on certain neurons of the central nervous system and the peripheral nervous system, helping to support the survival of existing neurons, and encourage the growth and differentiation of new neurons and synapses. Neurotrophins are proteins that help to stimulate and control neurogenesis, BDNF being one of the most active. Other examples of neurotrophins that can be employed include neurotrophin-3 (NT-3), neurotrophin-4 (NT-4), and nerve growth factor (NGF).

Once growth factor 44 is loaded, the pores 42 of polymer 40 are closed by changing the voltage on the nanorods 26.

Referring to FIG. 12, a nanodevice 50 can be placed in vivo by surgery or injection. Prior to in vivo placement, neuro stem cells 47 are loaded into a stimulation electrode region 35 of the device 50. The cells 47 can be attached using electrical charge or using a gel or other media. The neuro stem cells 47 are loaded when the polymer 40 has closed pores 42. The device 50 is then placed in vivo by a surgical procedure or by injection into a host. The neuro stem cells 47 can be stimulated electrically to cause growth.

As cells 47 interact with the surface of the device 50, the cells 47 can begin to grow to stimulate their differentiation into functional nerve cells. The amount and type of electrical stimulation can vary depending on the circumstances.

Figure 14:
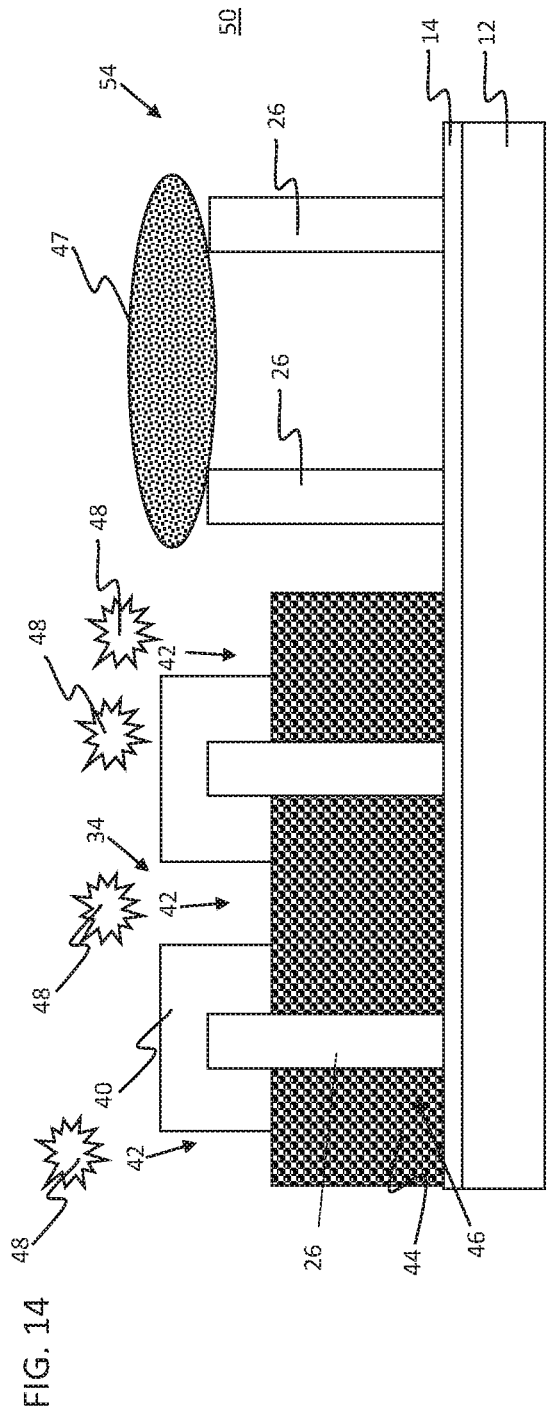
FIG. 14 is a cross-sectional view showing the substrate of FIG. 13 with stem cells being grown in vivo in accordance with an embodiment of the present invention.

Referring to FIGS. 13 and 14, electrodes (nanorods 26) in region 34 are activated to open the pores 42 of the polymer 40 to an open position. This permits growth factor 48 to be released through the pores 42. The growth factor 48 includes a dosage that will provide additional growth stimulation to the stem cells 47. The growth factor 48 promotes the growth of the cell or cells 47 increasing the size of the cell 47 as depicted in FIG. 14.

The opening of the pores 42 can be performed in a pulsatile (or on-demand) manner so that the release of growth factor 48 can be carefully controlled. A switching time of a few seconds or less can be employed to provide local and on-demand delivery of the growth factor 48. The pores 42 can be closed again by changing the voltage on the nanorods 26 in the polymer 40 until activated at a later time to stimulate cell growth or to treat a wound or other tissue.

Prior to placement of the device 50 in vivo, stem cells 47 are loaded in a cell loading region 54 of the device 50. The cell loading region 54 can include exposed or coated electrodes 26. The cells 47 can be loaded using a gel, liquid or other media to hold the cells in position during transport to a treatment area. The cells 47 can also be loaded using a static electrical charge on the electrodes 26 in the cell loading region 54. The device 50 can be placed in vivo to sense or measure concentrations of materials within the body (e.g., using designated nanorods 26 or other sensors). The device 50 can be set or moved to a particular location or locations within the body. The locations may include locations where nerve tissue is missing, damaged or destroyed.

When cells 47 are needed to treat or replace nerve cells, the cells 47 can be electrically stimulated to activate growth. During the growth cycle, reservoir 46, which is loaded with growth factor 44 (or inhibitor), can be selectively activated to release growth factor material to enhance or guide the growth of the cells 47. Inhibitor may be employed to slow the growth, if needed. Electrodes (nanorods 26) in region 34 are activated to open from the closed position depicted in FIG. 12 to release the growth factor 48. The growth factor 48 can stimulate growth including supporting the differentiation of stem cells into functional nerve cells.

It should be understood that the growth and differentiation of the stem cells 47 can be achieved by any combination of electrical pulses, growth factors, inhibitors and other stimulants applied in any advantageous sequence or sequences. The nanorods 26 in region 54 can, for example, have a spacing, e.g., between about 30 nm-2000 nm, such that a common voltage applied to all nanorods 26 results in an electric field between the nanorods. The electric field intensity can be controlled by adjusting voltage (e.g., between, e.g., about 0.01 volts to about 5 volts. It should be understood that electric field intensity can be adjusted in a plurality of ways. For example, the size, shape and density of the nanorods 26 can be controlled. In other embodiments, pulse shapes and pulse frequencies can be adjusted and controlled for pulsations of voltage or current to the nanorods 26. Other electric field intensity controls are also contemplated, e.g., nanorod coatings, such as, e.g., a porous protective coating, electrical insulating layers, etc. The voltage/electric field intensity can be controlled separately in different regions (e.g., region 34 and region 54).

For example, region 54 can permit electrical stimulation of neuro-stem cells 47, in place on the device 50. Cell 47 can be bound to nanorod electrodes 26 in region 54, which includes an electrical pulsation that stimulates cell growth. The cells 64 can be employed in a treatment program, e.g., in vivo. Growth stimulation can be provided in accordance with the present embodiments depending on the electrical settings and environmental conditions created.

Figure 15:
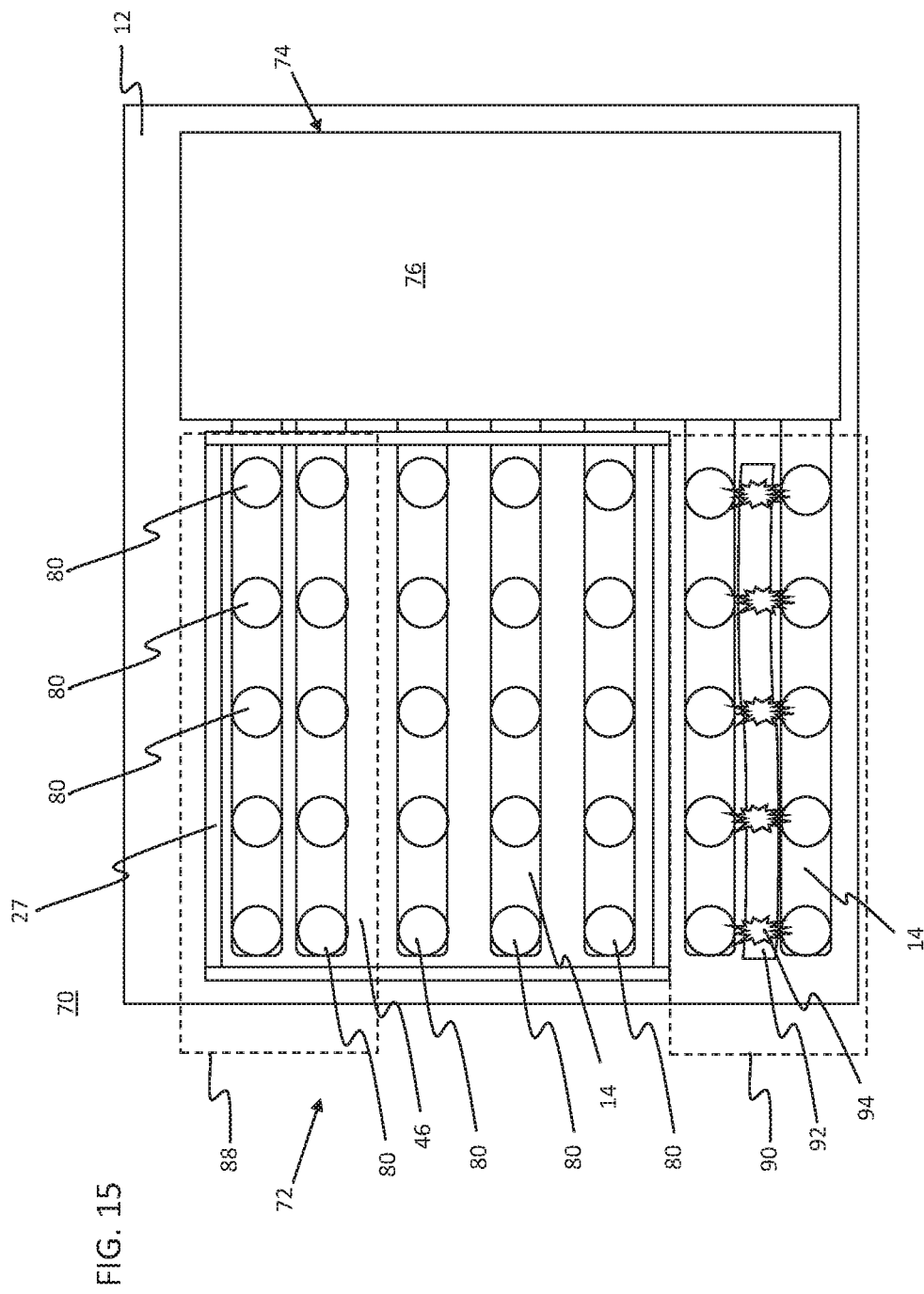
FIG. 15 is a plan schematic view showing a nanodevice having nanorods and circuits integrated on a substrate in accordance with an embodiment of the present invention.

Referring to FIG. 15, a device 70 for promoting stem cell growth is illustratively shown in accordance with one embodiment. The device 70 includes an array 72 of electrodes 80. The array 72 can include uniform spacings between electrodes 40; however, non-uniform spacings can also be employed. An illustrative encapsulation wall 27 is shown to form a reservoir 46. A circuit 74 can include an array of transistors and/or other circuit components (e.g., integrated into the substrate 12) configured to activate or selectively activate electrodes. The circuit 74 can be integrated into the substrate 12 using semiconductor processing techniques. The circuit 74 can include a power source, e.g., if the device 70 is implantable in the body. Alternatively, the circuit 74 can connect to a separate external power source.

The circuit 74 can be controlled using a controller circuit 76 that generates signals to control which and in what manner electrodes 80 are activated. The voltage can be programmed to activate the electrodes 80 using a patterned metal layer 14 to connect to the electrodes 80 in localized areas to affect cell growth over specific regions of the array 72 or the whole array 72. The activation of the electrodes can promote cell growth or selectively enable the release of growth factor in different regions of the device 70.

Device 70 can also include a biosensor that employs biological recognition properties for selective detection of various analytes or biomolecules. The biosensor 70 can generate a signal or signals that quantitatively relate to a concentration of the analyte on or near the electrodes 80. To achieve a quantitative signal, a recognition molecule or combination of molecules can be immobilized at the electrodes 80, which convert the biological recognition event into a quantitative response.

In some embodiments, the nanorod electrodes 80 can produce electrical fields for stimulating cell growth, releasing drugs or growth promoters or combinations of these tasks. The device 70 can oscillate between measuring cycles and cycles to promote cell growth. It should be understood that multiple reservoirs can be employed and separately controlled having a same or different payloads, as needed.

Device 70 can include regions with different spacings between nanorods 80 (e.g., region 88). Device 70 can include different cell growth promoting mechanisms and can include electrical based systems using spacings and electrical pulses to cause cell growth. The device 70 can be made disposable after use. The substrate 12 and other components can be coated or shielded to prevent contamination to the host from materials of the device 70.

In one embodiment, a cell loading region 90 (54, in FIG. 14) includes cells 94 suspended in a media 92 to load the cells 94 on the device 70. The device can be covered or sheathed to protect the cells 94 and media 92 during placement in vivo.

Figure 16:
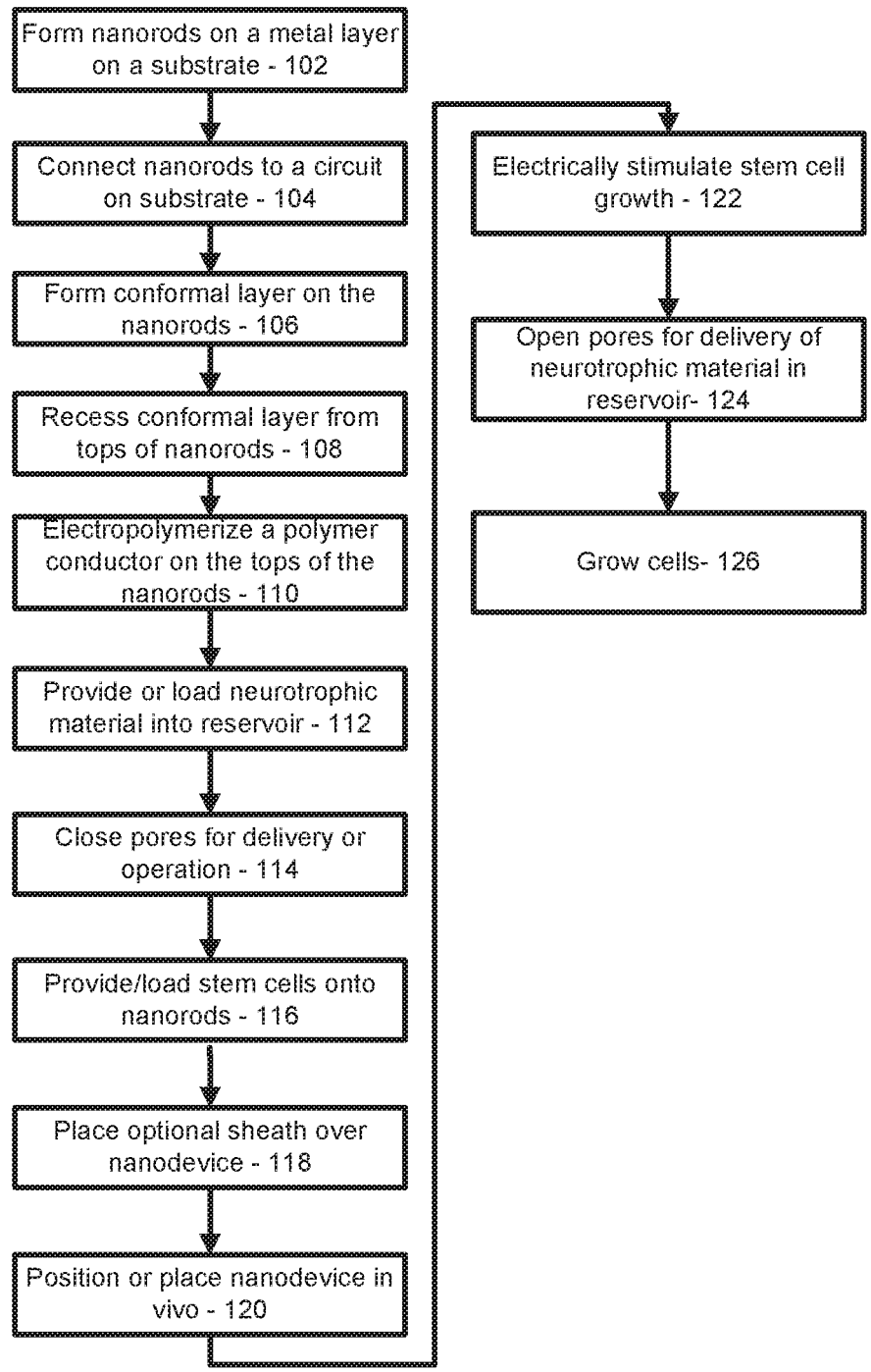
FIG. 16 is a block/flow diagram showing methods for fabricating and using a nanodevice in accordance with embodiments of the present invention.

Referring to FIG. 16, methods for fabricating a cell growth promoting or stem cell differentiating nanodevice are illustratively shown and described. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 102, nanorods are formed on a metal layer. The metal layer on which the nanorods are formed can be patterned to provide electrical connections to the nanorods or groups of nanorods.

In block 104, the nanorods can be connected to a circuit to provide selective activation of the nanorods as electrodes. The circuit can include an integrated circuit formed within the same substrate as the nanorods are formed on. Alternately, the circuit or chip can connect or be integrated with the substrate with the nanorods. Metal paths can be formed by patterning the metal layer on which the nanorods are formed.

In block 106, a conformal layer is formed over the nanorods by, e.g., atomic layer deposition by depositing layers of aluminum or silicon and oxidizing. It should be understood that while Si and Al are preferred materials, other materials or combinations can be employed to form a coating or membrane.

In block 108, the conformal layer is recessed in at least one region (e.g., over a portion of the nanorods). This can include patterning a hardmask over a portion of the device and etching a protective layer, e.g., OPL, until tops of the coated nanorods are exposed. The exposed tops are etched to remove the coating and expose the nanorods. The hard mask and OPL or other protective material can then be removed.

In block 110, a polymer conductor is electropolymerized on tops of nanorods (exposed by recessing) to form a reservoir between the electropolymerized conductor and the metal layer. The electropolymerized conductor includes pores that open and close responsively to electrical signals applied to the nanorods. The electropolymerized conductor can include polypyrrole, which can be doped with anions to be formed in its oxidation state.

In block 112, a cell growth affecting (promoting or inhibiting) dispensing material to be dispersed is loaded in the reservoir in accordance with open pores. The reservoir can be formed using a metal boundary, a dielectric boundary or any other suitable material that can be patterned in accordance with semiconductor formation processing. The dispensing material can include neurotrophic materials, such as, e.g., one or more neurotrophins. The pores are held open by applying an electric field to the electropolymerized conductor (e.g., using nanorods). The dispensing material is applied to the device and settles through the open pores to load the reservoir.

In block 114, the pores are then closed for in vivo delivery and operation using a voltage on the nanorods.

In block 116, cells, e.g., neuro-stem cells are provided or loaded onto nanorods in a cell loading region of the nanodevice. The cells are loaded using a media such as a gel or other liquid or can be held using a static electrical charge.

In block 118, a removable protective sheath can be placed over the nanodevice to permit delivery to an in vivo location. The sheath can be removed before nanodevice operation in vivo.

In block 120, the nanodevice is positioned in vivo or otherwise.

In block 122, an electrical charge is delivered and controlled to stimulate growth of the cells in vivo.

In block 124, the pores can be opened to dispense the dispensing material in accordance with electrical signals. The electrical signals can be pulsed to provide better control of an amount of dispensing material released. The dispensing material can include a cell growth promoter, drug, or other materials. In one embodiment, the dispensing material can include a growth factor, such as, e.g., a neurotrophic growth factor, to stimulate the growth of stem cells, or other growth factors, such as, e.g., hormones (e.g., steroids), cytokines, or other proteins and stimulants.

The nanorods can be grouped into a first region and a second region where the first region includes the electropolymerized conductor and dispenses material using electric fields on nanorods. A second region can include a cell growth region. The dispensing material can be dispersed two or more times by opening and closing the pores when needed.

In block 126, the cells are grown to differentiate the stem cells as nerve cells to replace missing or damaged nerve tissue.

Having described preferred embodiments for neuro-stem cell stimulation and growth enhancement with implantable nanodevices (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A nanodevice, comprising:
   an array of metal nanorods formed on a substrate, the array of metal nanorods being grouped into a first region and a second region;
   the first region including first nanorods such that upon activation of the first nanorods an electric field consistent with promoting stem cell growth is achieved; and
   the second region including second nanorods configured to activate an electropolymerized electrical conductor formed over tops of the second nanorods to form a reservoir between the electropolymerized electrical conductor and the substrate, the electropolymerized electrical conductor including pores that open or close responsively to electrical signals applied to the second nanorods to release a growth factor.

2. The nanodevice as recited in claim 1, wherein the electropolymerized electrical conductor includes electrically conductive polymers selected from the group consisting of polypyrrole, polyanilines, poly(thiophene), poly(3,4-ethylenedioxythiophene), poly(p-phenylene sulfide), poly(p-phenylene vinylene), poly(acetylene) and a combination thereof.

3. The nanodevice as recited in claim 1, wherein the substrate includes a semiconductor material and further comprises a control circuit formed in the substrate to control activation of the first and second nanorods.

4. The nanodevice as recited in claim 1, wherein the growth factor includes a neurotrophin.

5. The nanodevice as recited in claim 4, wherein the neurotrophin is selected from the group consisting of brain-derived neurotrophic factor (BDNF), neurotrophin-3 (NT-3), neurotrophin-4 (NT-4) and nerve growth factor (NGF).

6. The nanodevice as recited in claim 1, wherein the electrical signals on the second nanorods are pulsed to control an amount of the growth factor released.

* * * * *